United States Patent [19]

Shimada et al.

[11] 4,354,308
[45] Oct. 19, 1982

[54] METHOD FOR MANUFACTURE OF A SELECTIVE CHEMICAL SENSITIVE FET TRANSDUCER

[75] Inventors: Kiyoo Shimada, Kurashiki; Masayuki Matuo; Masayoshi Esashi, both of Sendai, all of Japan

[73] Assignees: Kuraray Co., Ltd., Okayama; Taoayuki Matsuo, Sendai, both of Japan

[21] Appl. No.: 118,774

[22] Filed: Feb. 5, 1980

Related U.S. Application Data

[62] Division of Ser. No. 957,433, Nov. 3, 1978, Pat. No. 4,218,298.

[30] Foreign Application Priority Data

Nov. 4, 1977 [JP] Japan .................................. 52-132679

[51] Int. Cl.$^3$ ............................................ H01L 21/22
[52] U.S. Cl. .................................... 29/571; 29/569 R; 29/583; 148/187; 204/195 B; 357/25
[58] Field of Search ...................... 29/569 R, 571, 583; 148/187; 204/195 B; 357/25

[56] References Cited

U.S. PATENT DOCUMENTS 4,020,830 5/1977 Johnson et al. ............... 204/195 B
4,218,298 8/1980 Shimada et al. ............... 204/195 P

OTHER PUBLICATIONS

Esashi et al., *J. of the Japan Soc. of Appl. Phys.*, vol. 44 (1975), pp. 339–343, 357–425.
Matsuo et al., *IEEE Trans. on Biomed. Eng.*, Nov. (1974), pp. 485–487.
Finne et al., *J. Electrochem. Soc.: Solid State Science*, Sep. 1967, pp. 965–970.
Moss et al., *Analytical Chemistry*, vol. 47, No. 13, Nov. 1975, pp. 2238–2243.
Janata et al., *Biomedical Engineering*, Jul. 1976, pp. 241–245.

*Primary Examiner*—G. Ozaki
*Attorney, Agent, or Firm*—Birch, Stewart, Kolasch & Birch

[57] ABSTRACT

A selective chemical sensitive field-effect transistor device for use in detection and measurement of chemical properties of substances to which the device is exposed is disclosed. The chemical sensitive FET device comprises a semiconductor substrate, at least one pair of spaced apart diffusion layers formed on one surface of the semiconductor substrate and forming source and drain regions, respectively, and a double layer structure consisting of a silicon oxide layer and an electrically insulating layer overlaying the silicon oxide layer. A gate region located on a portion of the surface of the semiconductor substrate between the diffusion layers is overlaid with a chemical selective membrane adapted to interact with certain substances. A method for the manufacture of the above described FET device is also disclosed.

5 Claims, 18 Drawing Figures

METHOD FOR MANUFACTURE OF A SELECTIVE CHEMICAL SENSITIVE FET TRANSDUCER

This application is a divisional of copending application Ser. No. 957,433, filed on Nov. 3, 1978, now U.S. Pat. No. 4,218,298.

BACKGROUND OF THE INVENTION

The present invention relates to a selective chemical sensitive FET transducer for use in detection and measurement of chemical properties, and a method for the manufacture of such selective chemical sensitive FET transducer. ("Chemical properties", as used herein, shall be understood to include ion activity and concentration, presence and concentration of enzymes, substrates, antibodies, antigens, hormones and reducible gases and the presence, concentration and activity of any of a variety of chemical and biochemical substances.)

As an instrument selectively sensitive to a chemical substance, such as hydrogen ions, sodium ions, potassium ions, calcium ions, oxygen gas and/or carbon dioxide gas, for detecting and measuring chemical properties of such substance, a positive ion sensitive glass electrode has heretofore been known. This glass electrode is, when used in the measurement of the ion activity such as often considered of prime interest in the medical or physiological field, inserted in a tissue of a living body.

Because of the nature of the manner in which the glass electrode is used, various attempts have heretofore been made to make it miniature. However, the manufacture of the glass electrode of a compact or miniature size involves the following shortcomings.

(a) Since the resistance of a glass film forming the glass electrode is about 10 megaohm, the use is required of an amplifier of a type having a high input resistance.

(b) Since the glass film is very thin, it lacks sufficient physical strength.

(c) Since the area of the glass membrane of a miniature glass electrode is small, the resistance of the glass electrode film correspondingly increases.

In view of the above, the required measurement instrument is bulky and complicated. Furthermore, not only is the glass electrode itself fragile and, therefore, susceptible to damage, but also various problems in practice have been involved when it comes to the use of the glass electrode in the tissue of the living body for detecting and measuring any substance present in such tissue of the living body.

In order to overcome the above described shortcomings of the conventional glass electrode, a recently developed solid-state measuring device is disclosed in "Development, Operation, and Application of the Ion-Sensitive Field-Effect Transistor as a Tool for Electrophysiology" by Piet Bergveld, IEEE Transactions of Biomedical Engineering, September, 1972, (Vol. BME 19, No.5), pages 342-351. The ion-sensitive field-effect transistor suggested by Piet Bergveld is a modified version of the conventional metal oxide semiconductor field-effect transistor (MOSFET) wherein a metallic plate forming the gate in MOSFET has been replaced by an electrically insulating layer of a silicon dioxide which is, when the device is in use for the measurement of ion activities in a solution, held in contact with the solution, to detect a potential difference between the solution and the insulated layer. The principle of the modified MOSFET suggested by Piet Bergveld is based on the fact that the conductivity of an electroconductive channel between the source and drain regions depends on the potential difference between the insulated-gate layer, that is, silicon dioxide insulation layer, and the solution. Because of the principle of the modified MOSFET, Piet Bergveld has made it possible not only to manufacture the measuring device in a miniature size without increasing the input impedance, but also to manufacture a solid-state measuring device of a type having a plurality of such transducers for enabling measurement of different chemical properties. In particular, the solid-state measuring device suggested by Piet Bergveld is, because of the smallness of its low output being impedance, generally considered an attractive and convenient instrument for a monitoring sensor which is used as inserted in the tissue of a living body during the physiological measurement. However, since the modified MOSFET has its insulated gate of the silicon dioxide, immersion of the device in the solution results in hydration of the silicon oxide insulation layer, therefore, the accuracy of the measurement of the ion activity tends to be adversely affected once such hydration takes place.

An improved version of the modified MOSFET has fairly recently been disclosed in "An Integrated Field-Effect Electrode for Bipotential Recording" by K. D. Wise et al., IEEE Transactions on Biomedical Engineering, November, 1974, (Vol. BME 21, No.6), pages 485-487. The device suggested by K. D. Wise et al. is similar to the above-described one, but for having a silicon nitride layer additionally formed on the insulated gate layer of silicon oxide. This device is successful in substantially eliminating the possibility of the hydration of the silicon dioxide layer, thereby enabling the accurate and effective ion activity measurement. This improved version is referred to as a liquid-oxide semiconductor field-effect transistor (LOSFET) and is useable as a sensor sensitive to hydrogen ions. In fact, K. D. Wise et al. have suggested in the same literature that the LOSFET can be used as a sensor selectively sensitive to any one of a number of some chemical substances and/or measuring various chemical properties.

The U.S. Pat. No. 4,020,830, patented on May 3, 1977, discloses a selective chemical sensitive FET transducer capable of selectively detecting and measuring chemical properties of substances to which the transducer is exposed. This chemical sensitive FET transducer has an insulated gate layer, such as silicon dioxide or silicon nitride, on which a chemical selective system adapted to interact selectively with certain ions, such as sodium ion, potassium ion and so on when exposed to a solution containing those ions, as in the case of the glass electrode, is overlaid.

However, in order for any one of the above described conventional FET transducers to be operable in a steady manner even when immersed in an aqueous solution to which it is exposed, the surfaces of the silicon substrate are defined by trimming the silicon wafer along the scribed lines during the manufacture of silicon nitride ($Si_3N_4$), and covered with a layer of epoxy resin. While the epoxy resin layer must have a relatively small thickness in order for the transducer to be assembled in a miniature size, the employment of the thin epoxy resin layer is susceptible to dielectric break down and, therefore, the transducer cannot be used in practice for a prolonged period of time. Moreover, the insulation by the use of the epoxy resin layer is for the purpose of experiments and cannot be employed in the manufacture of the transducer on a mass-production basis.

In an attempt to make it possible to manufacture a chemical sensitive FET transducer on a mass-production basis, two of the inventors of the present invention have successfully developed an attractive and convenient method for the manufacture of the chemical sensitive FET transducer which is disclosed in the Japanese Laid-open Patent Publication No. 25385/1978, laid open to public inspection on Mar. 9, 1978. The manufacturing method disclosed in the Japanese Laid-open Patent Publication is characterized in the employment of a photoetching technique to enable the FET transducer to be fabricated by the use of any known integrated circuit board manufacturing process in combination with the silicon etching process. More specifically, according to the method disclosed in the Japanese Laid-open Patent Publication, the photoetching technique is applied to form diffusion layer of drain, source, channel stopper and so, on one surface of a silicon wafer and a layer of silicon dioxide is subsequently deposited on the FET transducers followed by the formation of a layer of $Si_3N_4$.

Thereafter, respective portions of the $Si_3N_4$ and $SiO_2$ layers and silicon wafer are etched sequentially in the order given above to form, for example, a comb-shaped cutout portion in the silicon wafer and, subsequently, the resultant exposed surfaces of the silicon wafer, which define the cut-out portion referred to above, are coated with an insulation layer of silicon dioxide ($SiO_2$). Finally, a chemical selective membrane adapted to selectively interact with any particular ion is overlaid on the gate region, thereby providing complete selective etch chemical sensitive FET transducers. Since the silicon etching technique is employed in this method, the manufacture of the transducers can be effectively achieved in a miniature size and on a mass-production basis, and also insulation of the fine tip of each transducer can easily be achieved. Moreover, since this method does not require the coating of exposed surfaces of the silicon substrate adjacent the gate regions with an electrically insulating material such as epoxy resin, it is therefore especially suitable to manufacture miniature FET transducers.

However, it has been found that the FET transducer manufactured by the method of the Japanese Laid-open Patent Publication involves the following shortcomings.

(A) Since the method is such that, after the field-effect transistors have been fabricated on the silicon wafer, a portion of the silicon wafer adjacent to gate regions is cut out by the use of a chemical etching technique, there is a relatively great possibility that the gate defining insulation layer is likely to be damaged or deteriorated during said chemical etching process of the silicon wafer.

(B) Possibly because it is difficult to achieve a complete insulation by the oxide layer coated over such exposed surfaces of the silicon wafer as formed by trimming to provide separate transducers, the insulating property of the oxide layer tends to be deteriorated and/or an electric signal drift is susceptible to occur during the continued use of the FET transducer for a prolonged period of time.

(C) The FET transducer so manufactured tends to be affected by the temperature change and the extent to which they are affected by the temperature change varies from one transducer to another. For example, the FET transducer so manufactured is used in the medical and physiological field, in particular, for detecting and/or measuring chemical components such as hydrogen, sodium and potassium ions in the tissue of the human body as well as blood etc.

The detection of pH value down to one place of decimals (corresponding about 6 mV) is generally considered very important in the case of metabolic or respiratory acidosis or alkalosis, and the FET transducer so manufactured results in considerable amount of measurement error since they usually have a temperature coefficient within the range of 0.7 to 4.5 mV/°C. and, in most cases, within the range of 2 to 4 mV/°C. Therefore, the FET transducer involves a problem to be solved before it is applied in practice.

(D) Reproducibility of temperature coefficients of the transducers varies from one transducer to another and, therefore, their temperature compensation can hardly be achieved in practice.

SUMMARY OF THE INVENTION

Accordingly, the present invention has been developed in view to substantially eliminate the disadvantages and inconveniences inherent in the prior art measuring devices of a similar kind and has for its primary object to provide an improved selective chemical sensitive FET transducer of a type capable of exhibiting an accurate and stable performance during the measurement of chemical properties.

Another important object of the present invention is to provide an improved selective chemical sensitive FET transducer of the type referred to above, wherein the dependence of the gate voltage on the temperature is very small and, therefore, there is a relatively high reproducibility of the temperature coefficient.

A further object of the present invention is to provide an improved selective chemical sensitive FET transducer of the type referred to above, wherein no voltage break down will occur during the measurement.

A still further object of the present invention is to provide an improved selective chemical sensitive FET transducer of the type referred to above, which can be manufactured at a relatively high yield and on a mass-production basis.

It is a related object of the present invention to provide an improved method for manufacturing the selective chemical sensitive FET transducer of the type referred to above.

It is another related object of the present invention to provide an improved method for manufacturing the selective chemical sensitive FET transducer of the type referred to above, which can produce a high yield.

According to the present invention, the selective chemical sensitive FET transducer herein disclosed is an insulated-gate field-effect transistor. This insulated-gate field-effect transistor is manufactured by forming an FET on a silicon wafer, cutting a portion of the silicon wafer adjacent gate regions, by the use of a chemical etching technique, rendering these regions of the silicon wafer to assume a substantially elongated needle-like shape, and finally trimming the silicon substrate to provide separate insulated-gate fieldeffect transistor transducers.

The insulated layer of gate region of each of the FET devices according to the present invention is composed of a double layer structure consisting of a layer of silicon dioxide ($SiO_2$) and a layer of one of silicon nitride ($Si_3N_4$) titanium oxide and alumina ($Al_2O_3$) aluminum oxide, the second-mentioned layer having an excellent electric insulating property and a sufficient resistance to chemical substances contained in a solution to which the device is exposed. Furthermore, the FET device according to the present invention may have a multi-layer structure consisting of the silicon dioxide layer, the electrically insulating and chemically resistant layer, and a chemical selective membrane which may be either an organic membrane or an inorganic membrane and which can selectively interact with particular chemical substances contained in a solution to which the device is exposed.

Moreover, the FET device according to the present invention may have an additional coating layer of organic semipermeable material for the purpose of avoiding any possible adherence of impurities or foreign matters to the gate region during the practical use of the device.

In any event, the FET device according to the present invention has its essential feature in the employment of the double layer structure, consisting of the silicon dioxide layer and the electrically insulating and chemically resistant layer, overlaying the surface as well as the side face of the cut-out portion adjacent the gate region. Preferably, the material for the electrically insulating and chemically resistant layer is silicon nitride.

Another important feature of the present invention resides in that, in order to improve the water proof and the electrically insulating property of the silicon dioxide layer overlaying the silicon substrate of the cut-out portion adjacent to the gate region as well as the entire surface area of the FET transducer, the electrically insulating and chemically resistant layer of, for example, silicon nitride is employed externally of the silicon dioxide layer. In the transducer of the construction according to the present invention, the temperature dependence of the gate voltage is small, for example, not more than 2 mV/°C. and generally less than 1 mV/°C. and, accordingly, in most cases during actual measurement of the chemical properties of substances, no temperature compensation is required. Moreover, the reproducibility of the temperature dependence is excellent.

The FET transducer having the double layer structure of the silicon dioxide layer and the electrically insulating layer, as hereinbefore described, can be used as a device responsive to pH value. However, the employment of the chemical selective membrane, such as employed in the conventional electrode, which interacts selectively with particular chemical substances and which overlays the double layer structure in accordance with the present invention, makes it possible to provide the transducer with the capability of selectively detecting and measuring the chemical properties of various substances to which it is exposed. The chemical selective membrane employed in the present invention may be either an inorganic membrane, made of, for example, alkali metal silicate glass, or an organic membrane containing a ligand capable of adsorbing a particular chemical substance. As an alkali metal a silicate glass, a composition containing $SiO_2$, $CaO$ and $Na_2O$ in a mol ratio of 72.2:6.4:21.4 may be employed. The FET device wherein the chemical selective membrane is composed of the inorganic membrane is effective to detect and measure hydrogen ions, sodium ions and potassium ions.

The ligand capable of adsorbing a particular chemical substance, which is employed in the organic membrane for the chemical selective membrane, includes an antibiotic, such as valinomycin or nonactin, and a cyclic ligand such as crown ether (mono-cyclic poly ether) or cryptant (bicyclicdiaza-poly ether). The organic membrane referred to above may be the one prepared from polyvinyl chloride, celluloses, polyurethane or polystyrene, with or without the addition of any suitable plastizer. A membrane made of palladium, or including of an antibody, homo or silver halide may also be used as the chemical selective membrane in the practice of the present invention. In particular, the use of palladium, antibody, homo layer or silver halide for the chemical selective membrane in the transducer of the present invention renders such transducer to be sensitive to hydrogen gas, antigens, oxygen gas, and halide ion respectively.

If the transducer according to the present invention is of a construction wherein the insulated-gate field-effect transistor is rigidly installed within an elongated tube with its gate region spaced from a gas-permeable membrane, secured to one open end of the tube, by the intervention of an electrolyte-containing porous filler material or an electrolyte-containing solution, such transducer can be used as a sensor for detecting and measuring chemical properties of a gaseous body. For example, in this construction, if a silver/silver chloride (Ag-/Agcl) electrode as a reference electrode and pH sensitive FET transducer is impregnated in an electrolyte containing $NaHCO_3$ and $NaCl$ each in an amount of 0.05 mol and being filled substantially hermetically between at least the gate region, reference electrode and the gas permeable membrane and the gas-permeable membrane is composed of a film of water-proof synthetic resin such as silicone rubber, the transducer sensitive to carbon dioxide can be obtained.

Yet, if the gate region of the transducer sensitive to the above described ions, gases or chemical substances is further overlaid with a chemical reaction layer capable of producing a particular reaction product, such as ion, gas or chemical substance, when reacting a certain chemical substance, a transducer suited for various other purposes can be obtained. By way of example, if the gate region of the FET transducer sensitive to pH is overlaid with a hydrophilic gel immobilizing glucose oxidase, the transducer sensitive to glucose can be obtained. This is because, the glucose oxidase oxidizes the glucose, diffused in the hydrophilic gel, to form a gluconic acid, and the gate region can detect and measure resulting change in pH. It is to be noted that the above described enzyme reaction consumes oxygen ($O_2$) as another reactant and, therefore, a similar measurement can be carried out by the use of a $PO_2$ sensitive FET transducer in place of the pH sensitive FET transducer. As the hydrophilic gel, any membrane can be used if it can fix the enzyme at the gate region and diffuse a substrate to the gate region. Examples of this hydrophilic gel are those of polyvinyl alcohol and natural protein. The hydrophilic gel may be employed in the form of two or more layers so that the enzyme reaction can take place in a multi-stage.

As one application of the present invention, a chemical sensitive FET transducer simultaneously sensitive to a plurality of different chemical substances can be obtained if two or more gate regions are formed on a single silicon substrate and different chemical selective membranes are overlaid on such gate regions.

The present invention also provides a method of manufacturing the above described chemical sensitive FET transducer. In one embodiment of the method of the present invention, after insulated-gate field-effect transistors have been formed on a common silicon wafer, a portion of the silicon wafer adjacent the subsequently formed gate regions, one for each transistor, is cut out by the use of a chemical etching technique to form a substantially comb-shaped cut-out portion in the wafer and, subsequently, the double layer structure consisting of the silicon dioxide layer and the electrically insulating layer of, for example, silicon nitride, is deposited on the entire surface area of portions of the silicon wafer where the respective gate regions are located.

In another embodiment of the method of the present invention, the above described cutting by the use of the chemical etching technique may be effected before the FET transistors are formed on the common silicon wafer. In this case, the formation of the FET transistors on the common wafer must be carried out prior to the formation of the double layer structure.

In either case, subsequent to the formation of the double layer structure on the silicon wafer, chemical selective membranes may be applied on the respective gate regions externally of the electrically insulating layer overlaying the silicon nitride layer.

The manufacturing method according to the present invention involves the following advantages.

(1) The manufacturing method is simple and is suited for the production of the chemical sensitive FET transducer on a mass-production basis.

(2) A portion of the FET transducer remote from the gate region can have a relatively large thickness and, therefore, the FET transducer as a whole can have a sufficient physical strength.

(3) The tip of the FET transducer adjacent the gate region may be made thin as desired by the use of a chemical etching technique.

(4) Since the cut-out portion of the FET transducer adjacent the gate region has the double layer structure of a silicon dioxide layer and an electrically insulating layer, a substantially complete electrical insulation can be realized.

(5) Since the gate insulation layer is formed subsequent to the chemical etching of the silicon wafer, the resultant FET transducer involves no possibility of forming defects and doping by impurities or foreign matter and the method does not substantially provide variation in quality of the transducers.

The chemical sensitive field-effect transistors of the present invention are arranged in a substantially comb-shaped configuration with a gate region of each of the transistors spaced a distance from regions of contact with source, drain and substrate electrodes. In addition, the silicon surface exposed when and after the common silicon substrate has been trimmed to provide the separate transistors, is limited to the vicinity of the respective contact regions to which bonding lead wires are connected.

Accordingly, as compared with the conventional similar method suggested by K. D. Wise et al. which requires a step of forming an electrically insulating layer over the exposed surfaces of the silicon surface on the trimmed side face without spoiling the gate region, the method of the present invention is greatly improved with respect to manufacturing the chemical sensitive FET transducer.

BRIEF DESCRIPTION OF THE DRAWINGS

These and other objects and features of the present invention will become apparent from the following description taken in conjunction with the preferred embodiments with reference to the accompanying drawings, in which:

FIGS. 5A to 5K are illustrative of the sequential steps of the method according to the present invention, wherein FIGS. 5A to 5D and FIGS. 5H to 5K are cross sectional views taken along the line 5—5 in FIG. 1, FIGS. 5E and 5G are perspective views, and FIG. 5F is a cross sectional view taken along the line 5F—5F in FIG. 5E;

FIG. 6 is a longitudinal sectional view of a chemical sensitive field-effect transistor transducer assembled in the form ready for the actual measurement of chemical properties of substances to which it is exposed;

FIG. 7 is an explanatory diagram showing an electrical circuit system used with the transducer manufactured according to the present invention.

DETAILED DESCRIPTION OF THE INVENTION

Figure 1:
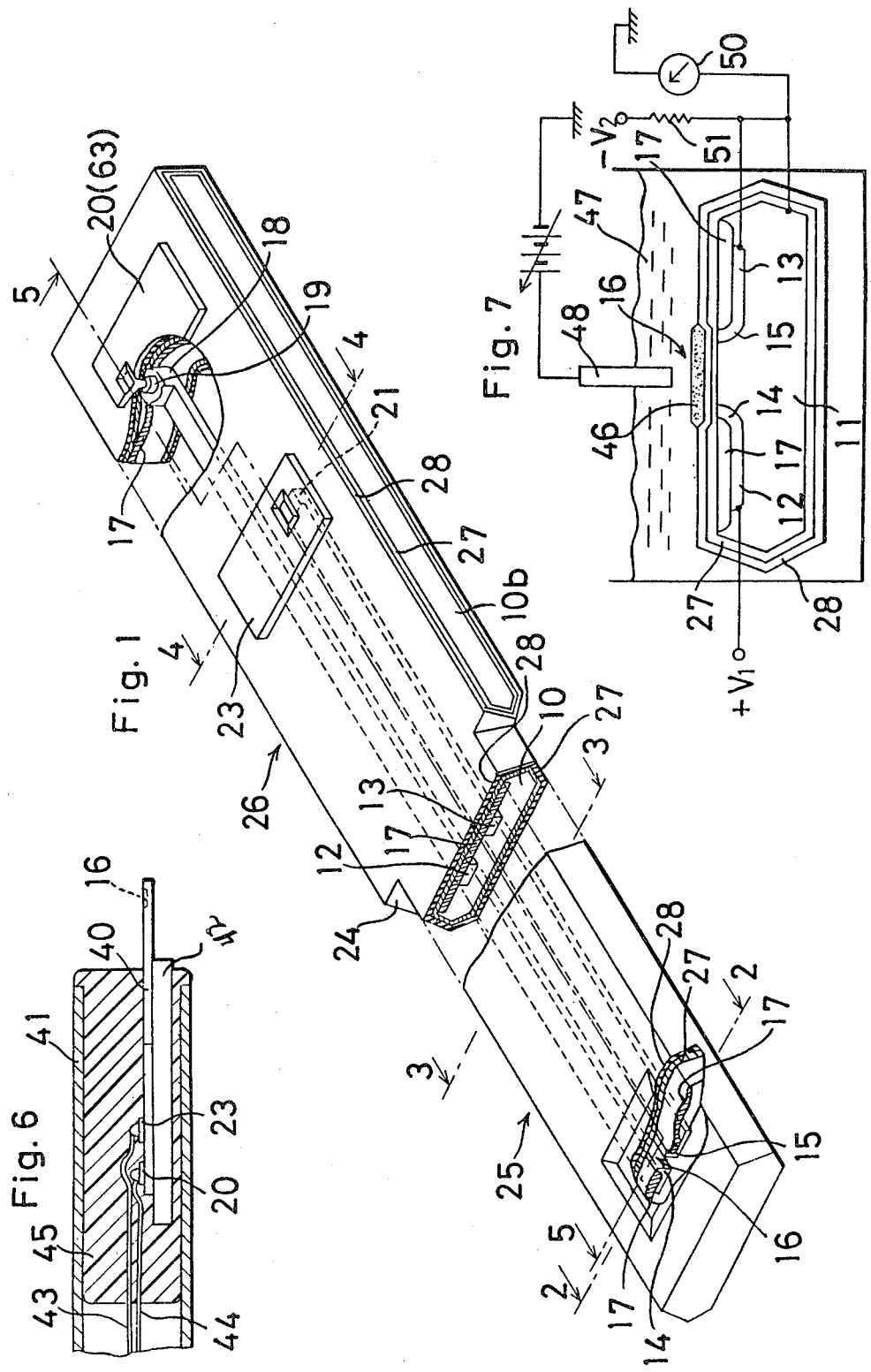
FIG. 1 is a perspective view, with a portion broken away, of a selective chemical sensitive FET transducer embodying the present invention.

Before the description of the present invention proceeds, it is to be noted that like parts are designated by like reference numerals throughout the accompanying drawings. It is also to be noted that, for the purpose of description of the present invention, the present invention will be described as applied to a hydrogen ion sensitive FET transducer.

Figure 2:
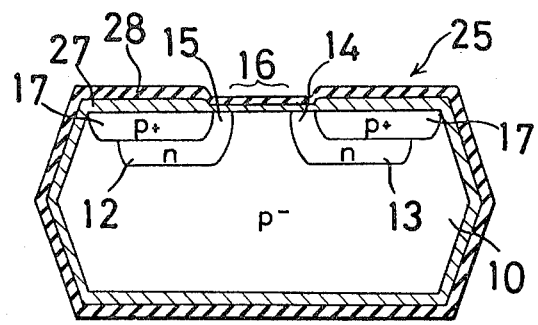
FIG. 2 is a cross sectional view, on an enlarged scale, taken along the line 2—2 in FIG. 1.

Referring first to FIG. 1, the hydrogen ion sensitive FET transducer embodying the present invention and illustrated therein comprises an elongated semiconductor substrate 10 made of a single crystal of silicon having a $p^-$-type doping polarity. This semiconductor substrate 10 has an upper surface formed with elongated diffusion regions 12 and 13 spaced a distance within the range of 50 to 100 microns from each other and extending in parallel to each other in a direction lengthwise of the silicon substrate 10 at a position intermediately of the width of the silicon substrate 10. These diffusion regions 12 and 13 have a doping polarity opposite to that of the silicon substrate 10, that is, a n-type doping polarity, and are formed at one end into the source and the drain, respectively. A surface region of the silicon substrate 10 located between the diffusion regions 12 and 13 is formed as a gate 16 as best shown in FIG. 2 in its cross-sectional representation.

Figure 3:
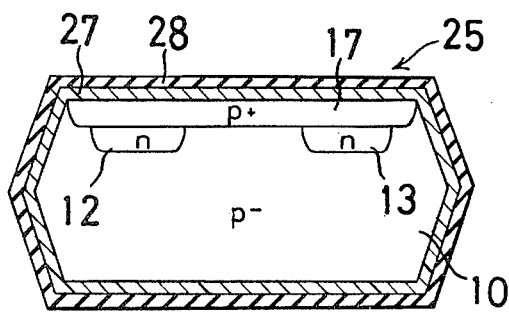
FIG. 3 is a cross sectional view, on an enlarged scale, taken along the line 3—3 in FIG. 1.

As best shown in FIG. 3, a $p^+$ channel stopper layer 17 is formed on the upper surface of the substrate 10 except for the gate region 16 (shown in FIG. 2) and overlays portions of the diffusion regions 12 and 13, but not the gate region 16, and contacts regions 19 and 22, so that no electric conductive channel will be formed between these diffusion regions 12 and 13 except at the gate region.

Figure 4:
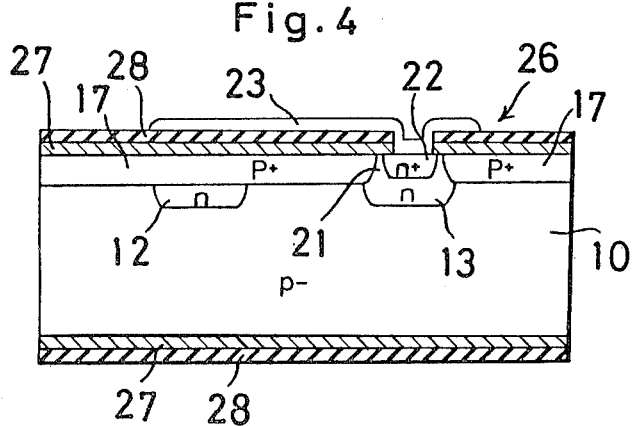
FIG. 4 is a cross sectional view, on an enlarged scale, taken along the line 4—4 in FIG. 1.

The other end 18 of the elongated diffusion region 12 is electrically connected to a source electrode 20, made of aluminum, through a n+ contact region 19 while the other end 21 of the elongated diffusion region 13 is, as best shown in FIG. 4, electrically connected to a drain electrode 23, made of aluminum, through an n+ contact region 22. It is to be noted that the source electrode 20 itself concurrently serves as a substrate electrode 63 made of aluminum.

Referring still to FIG. 1, the silicon substrate 10 is of a substantially T-shaped configuration stepped at 24 to have a reduced width section 25, in which the source 14 and the drain 15 are located, and a large width section 26 in which the source and drain electrodes 20 and 23 are located. The entire surface area of the silicon substrate 10 except the opposed side surfaces of the large width section 26 of the silicon substrate 10 as can readily be seen from FIG. 4, is covered with a double layered structure consisting of a layer 27 of silicon dioxide ($SiO_2$) and a layer 28 of silicon nitride ($Si_3N_4$).

The method of manufacturing the hydrogen ion sensitive FET transducer of the construction described above will now be described with reference to FIGS. 5A to 5K in the sequence of various steps of the manufacturing method.

(I) Formation of Insulated-gate FET Structure (i) Wet Oxidation

Figure 5A:

The wafer 11 made of silicon having a p-type doping polarity is, after having been washed, chemically etched out to have a uniform predetermined thickness. The silicon wafer 11 of uniform thickness is, after having been scribed to a predetermined size, oxidized at 1,150° C. for 30 hours under a wet atmosphere so that a layer 29 of silicon dioxide, about 6,000 Å in thickness, can be formed on the entire surface area of the silicon wafer as shown in FIG. 5A.

(ii) Photoetching

Figure 5B:
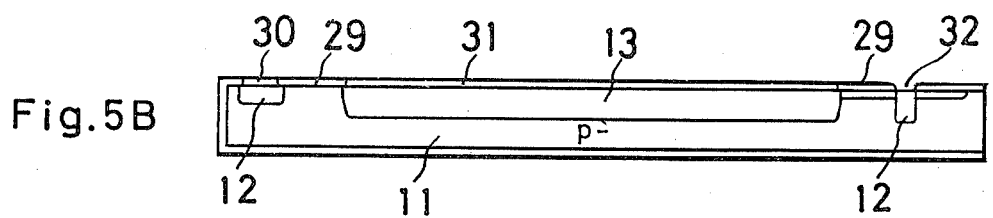

By the use of any known mask alignment device, a pattern (not shown) for the formation of the source and drain diffusion regions and a mask alignment pattern (not shown) are formed on the opposed surfaces of the silicon wafer 11 and are, after masks are applied to the silicon wafer 11 in alignment of these patterns, exposed to rays of light. Thereafter, by the use of a known photoetching technique, portions of the $SiO_2$ layer 29 are etched out to provide windows 30, 31 and 32 as shown in FIG. 5B.

(iii) Formation of n-type Source and Drain

The source and drain diffusion regions 12 and 13 are formed by predepositing phosphorous on the silicon wafer 11 through the windows 30, 31 and 32 and, then, heat-treating at 1,200° C. for 13 hours under a dry atmosphere to cause the phosphorus to diffuse into the silicon wafer 11 in a depth of 10 μm at a surface concentration of $N_a$ $10^{18}/cm^3$.

(iv) Diffusion of p+-type Channel Stopper Layer

Figure 5C:
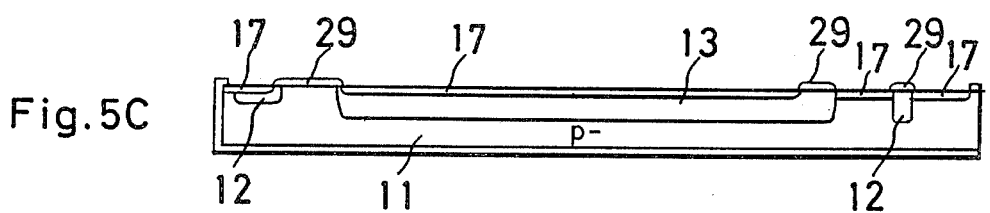

By using a pattern for the formation of the p+-type channel stopper, the silicon dioxide layer 29 is photoetched and boron is subsequently diffused to form the channel stopper layer 17 as shown in FIG. 5C. The diffusion of boron to form the layer 17 is carried out by heating at 1,100° C. for 10 minutes and then heat-treated at 1,150° C. and wet-atmosphere for 20 minutes.

(v) Diffusion to Form Contact Regions

Figure 5D:
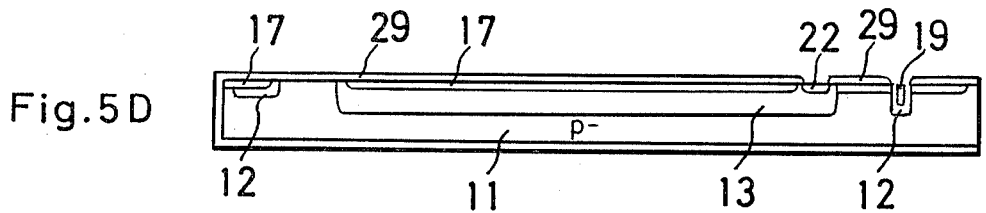

By the use of a pattern for the formation of n+ contact regions, the photoetching technique is employed to form diffusion layers 12 and 13 at respective positions where the source and drain electrodes are to be installed, in a manner as shown in FIG. 5D. This can be done by predepositing phosphorus at 1,100° C. and then heat-treating for 30 minutes at 1,200° C. under a wet atmosphere.

(II) Cut-out Process (i) Etching of $SiO_2$ Layer

Figure 5E:
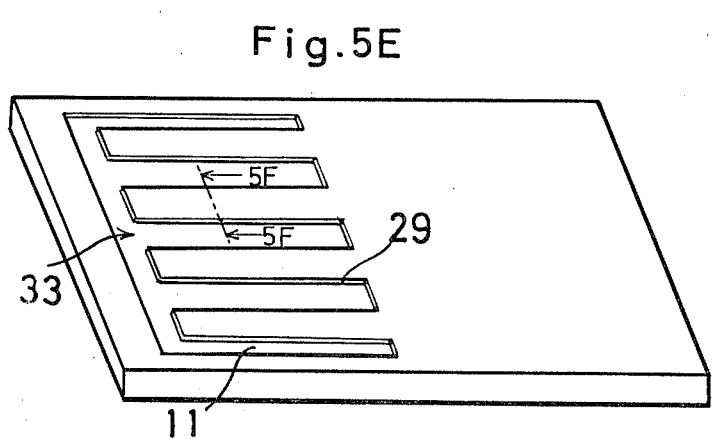

By the use of a comb-shaped pattern, respective portions of the $SiO_2$ layer 29 overlaying the silicon wafer 11, which are to be cut out, are etched out in a manner as shown by 33 in FIG. 5E.

(ii) Etching of Silicon wafer

Figure 5F:
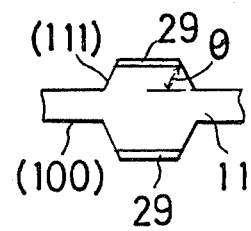
Figure 5G:
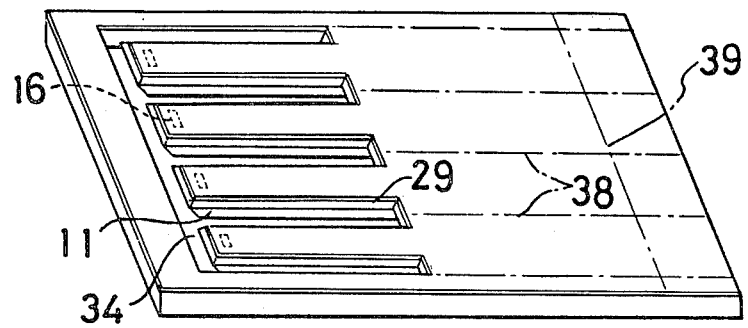

After the $SiO_2$ layer 29 has been etched out in the manner described above, a corresponding portion of the silicon wafer 11 is etched out by the use of an aqueous solution of amine (Composition: 17 cc ethylene diamine, 3 gr. pyrocatechal and 8 cc water). There, the opposed surfaces of the silicon wafer 11 are etched out in a manner as shown in FIG. 5F to form a substantially comb-shaped cut-out portion 34 as shown in FIG. 5G, which cut-out portion 34 is complementary in shape to the comb-shaped pattern 33 shown in FIG. 5E. The use of the aqueous solution of amine for etching is advantageous in that, while $SiO_2$ layer 29 which concurrently serves as a mask is not etched out, only the silicon wafer 11 of a relatively great thickness, for example, 150 μm, can be etched out. The speed of etching of the silicon wafer 11 varies depending on the orientation of the crystallographic axis of the single crystal of silicon which is a material for the silicon substrate 11, and the etching can be done far more readily in the (100) and (110) planes of the wafer 11 than in the (111) plane of the same wafer 11. Therefore, if the p⁻-type (100) silicon wafer is used for the silicon wafer 11, the reduced width sections 25 (FIG. 1) can precisely be obtained with no substantial formation of side edges. FIG. 5F illustrates a cross section of one of the reduced width sections 25 of the silicon wafer 11, which is employed for the purpose of explanation of the dependence of the etching solution on the orientation of the crystallographic axis. If the p⁻-type (100) silicon wafer is employed for the silicon wafer 11, the etching speed is low and the angle of inclination shown by θ becomes about 55° It is to be noted that, although the silicon wafer 11 has been described as etched out from both surfaces thereof, it may be etched out from one of the opposed surfaces thereof.

Figure 5H:
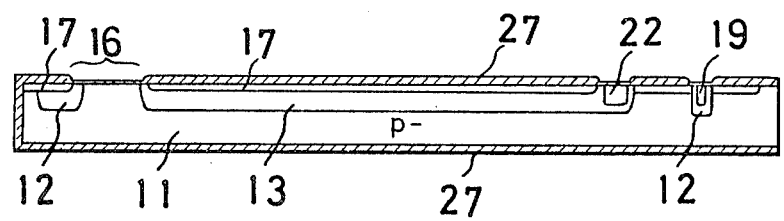

(III) Insulation of Gate Region and Wafer Side Faces (i) Oxidization and Photoetching Side faces of each of the reduced width sections 23 of the silicon substrate 11, which have been exposed subsequent to the etching of the silicon wafer 11 as shown in FIG. 5G, are heat-treated at 1,200° C. for 30 minutes under a wet atmosphere to form the layer 27 of silicon dioxide as shown in FIG. 5H and described with reference to FIG. 1. Subsequently, by the use of a mask, portions of the $SiO_2$ layer 27 overlying the gate region 16 and the contact region 19, respectively, are removed by photoetching. During this process of photoetching, the lower, or back surface of the silicon wafer 11 may be contacted with a Bakelite plate by the use of an electrowax for the protection of the $SiO_2$ layer covering the back surface of the silicon wafer 11 from being unnecessarily etched.

(ii) Dry Oxidation

By oxidizing the entire surface area of the silicon 11 under a dry atmosphere, the $SiO_2$ layer of 1,000 Å in thickness is formed thereon. The $SiO_2$ layer is the one which has been shown by 27 and described with reference to FIG. 1. The formation of this $SiO_2$ layer is carried out by heat-treating at 1,150° C. for 30 minutes under a dry atmsophere.

(iii) CVD of $Si_3N_4$ Layer and $SiO_2$ Layer

Figure 5I:
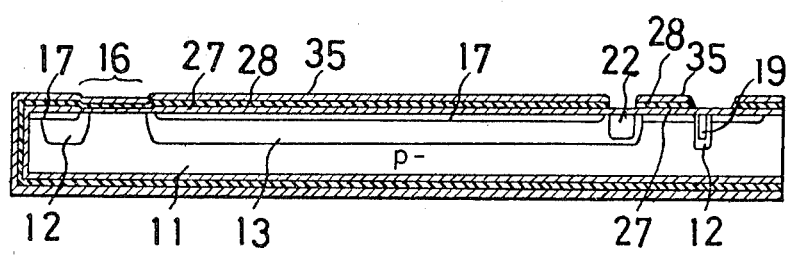

The layer of silicon nitride ($Si_3N_4$) of 1,000 Å in thickness, shown by 28 in FIG. 1, and the layer of silicon dioxide of 1,000 Å in thickness shown by 35 in FIG. 5I are formed on the silicon wafer 11 externally of the $SiO_2$ layer 27 by the use of a conventional chemical vapor deposition method (CVD method).

(IV) Etching Process

Subsequently, the photoetching is subjected in the following sequence by the use of a mask having a pattern for the formation of the contact regions as shown in FIG. 5I.

(i) Etching of $SiO_2$ Layer

By the use of a pattern for etching the $Si_3N_4$ layer 28 to define the contact regions 19 and 22, the etching is subjected to portions of the $SiO_2$ layer 35 which are respectively aligned with portions of the pattern for the contact regions, as shown in FIG. 5I. During the etching of the $SiO_2$ layer 35 in this manner, a Bakelite plate may be applied to the wafer 11 by the use of an electrowax in such a manner as to cover the cutout portion 34 (FIG. 5G) adjacent the gate regions 16 in the respective reduced width sections 25 for the purpose of protection of the gate regions 16 and the back surface.

(ii) Etching of $Si_3N_4$ Layer

As shown in FIG. 5I, the $Si_3N_4$ layer 28 is etched out by the use of hot-aqueous phosphoric acid. It is to be noted that, for this purpose, any known plasma etching technique may be employed. Where the plasma etching technique is employed, the step of formation of the $SiO_2$ layer 35 by the CVD method and the step described under the heading of IV-(i) are not necessary.

(iii) Etching of $SiO_2$ Layer

Figure 5J:
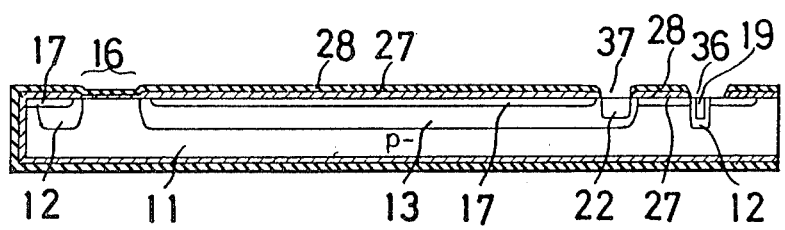

After the $SiO_2$ layer 35 and the portions of the $SiO_2$ layer 27 corresponding in position to the contact regions have been etched out by the use of a HF type etching solution, the windows 36 and 37 of the contact regions 19 and 22 can be formed as shown in FIG. 5J.

(V) Electrode Formation

Figure 5K:
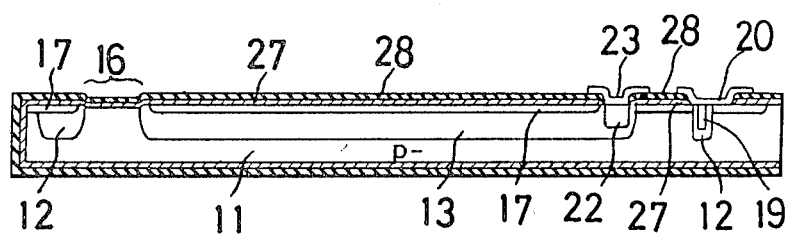

Aluminum is vapor-deposited by the use of a mask having a pattern, complementary in shape to the electrodes, to form the electrodes 20 and 23 electrically connected respectively to the source region 12 and the drain region 13, as shown in FIG. 5K. The wafer 11 having the electrodes 20 and 23 deposited thereon is subsequently heat-treated at 500° C. for the purpose of improving the bondability of each of the electrodes 20 and 23 to the contact regions 19 and 22.

Although the source electrode 20 so formed has been described as concurrently serving as an electrode 63 electrically connected to the silicon wafer, it will readily be seen to those skilled in the art that the source electrode 20 and the substrate electrode 63 can be formed separately.

(VI) Trimming, Installation and Wiring

The silicon wafer is, after the completion of the foregoing process step, trimmed by the use of a scriber along respective trimming lines, shown by 38 and 39 in FIG. 5G, to provide individual ion sensitive FET devices, each being of a construction shown in FIG. 1.

The device 40 so manufactured is, for example, as best shown in FIG. 6, rigidly mounted on a support 42 with lead wires 43 and 44, respectively, connected to the drain electrode 23 and the source and substrate electrode 20(63) by the use of silver paste. The assembly is then inserted in an elongated tube 41 and fixed in position within said elongated tube 41 by means of a filler material 45, which may be an epoxy resin and which is filled within the tube 41, in such a manner that a portion of the device 40 remote from the gate region 16 is completely embedded in the filler material 45 together with the lead wires 43 and 44. Where the connection of the lead wires 43 and 44 to the drain electrode 23 and the source electrode 20, respectively, is desired to be effected by means of a known soldering technique, it is preferable that the surface of each of the drain and source electrodes 23 and 20 be vapor-deposited with electroconductive layers of Cr, CrCu and Cu.

Each of the hydrogen ion sensitive FET devices 40 manufactured in accordance with the present invention in the manner hereinbefore described has a double layered structure, consisting of the $SiO_2$ layer 27 and the $Si_3N_4$ layer 28, which double layered structure covers the substantially entire surface area of the silicon substrate 10 except for the trimmed side faces 10b of the large width section 26 which are exposed as best shown in FIG. 1. Accordingly, subsequent to the connection of the lead wires 43 and 44 to the drain electrode 23 and the source electrode 20, described with reference to FIG. 6, the trimmed side faces 10b of the silicon substrate 10 should be electrically insulated. The requisite insulation of the trimmed side faces 10b of the silicon substrate 10 is, in the instance so far described and illustrated, achieved by the filler material 45 which encloses completely the large width section 26 of the silicon substrate 10 and which concurrently serves as an electric insulator.

With this device 40, namely, the hydrogen ion sensitive FET transducer, so manufactured in the manner described above, voltage breakdown will not occur during a prolonged period of use and the temperature coefficient of such a device has been found to be about 0.4 mV/°C. at pH 7. This means that the hydrogen ion sensitive FET transducer manufactured according to the present invention has been found to be satisfactorily and effectively used in the field of medical and physiological fields.

It is to be noted that, if a chemical selective membrane 46 which interacts with particular chemical substances is applied to the gate region 16 at a position externally of the $Si_3N_4$ layer 28 in a manner as shown in FIG. 7, the transducer sensitive to chemical properties other than the pH value can be manufactured. This will now be described with particular reference to FIG. 7.

Referring now to FIG. 7, the chemical selective membrane 46 may be composed of one of palladium, antimony, silver halide and so on. During the measurement by the use of the transducer manufactured according to the present invention, the chemical selective membrane 46 is, as best shown in FIG. 7, adapted to contact a solution 47. In practice, to enable the transducer 40 to detect and measure chemical properties of the solution 47 to which the chemical selective membrane 46 is exposed, a reference electrode 48 is employed for applying a reference voltage to the solution 47. In the instance as shown, this reference electrode 48 is electrically connected to the ground so that a zero reference voltage can be applied to the solution 47 through such reference electrode 48. On the other hand, the drain electrode 20 and both of the source electrode 23 and substrate electrode 63 are respectively electrically connected to a positive power source $+V_1$ and a negative power source $-V_2$, in a manner as shown in FIG. 7, so that an electric current can flow from the drain region 15 to the source region 14 through the electroconductive channel to thereby develop a potential difference across the electroconductive channel. A voltmeter 50 is electrically connected in such a way as to measure the drain current flowing from the drain electrode.

If the transducer of the construction shown in FIG. 1 is used in such a manner that, as best shown in FIG. 7, the chemical selective membrane 46 is exposed to the solution 47 containing ions to which such chemical selective membrane 46 interacts selectively, this transducer can operate in a similar manner to the operation of the known metal oxide semiconductor field effect transistor (MOSFET). More specifically, when the reference electrode 48 is suitably biased, the chemical selective membrane 46 interacts with the ions, contained in the solution 47 to which it is exposed, this results in a development of a potential difference between the chemical selective membrane 46 and the solution 47. This in turn results in development of an electric field in the electroconductive channel, the intensity of which varies depending upon the concentration of the ions contained in the solution 47 and affects the conductivity of the channel. When the transducer is used in such a manner as shown in FIG. 7, the potential difference between selective chemical sensitive layer 46 and substrate 10 is kept to be constant by using resistor 51. Accordingly, the surface potential of the layer 46, which depends on concentrations or properties of chemical substances, may be obtained by the reading of volt meter 50 where the reading of volt meter 50 is the sum of potential difference between the layer 46 and substrate 10 and that between layer 46 and the solution 47, the latter potential difference being determined by concentration of any chemical substance in solution 47.

Where no chemical selective membrane such as shown by 46 is employed, that portion of the $Si_3N_4$ layer 28 which overlays the gate region 16 serves to measure the concentration of hydrogen ions when exposed to such solution 47. It is to be noted that, since the $Si_3N_4$ layer 28 overlays completely that portion of the $SiO_2$ layer 27 which in turn overlays the gate region 16, there is no possibility of electrical short circuiting between the silicon substrate 10 and the solution 47 which may otherwise take place when the $SiO_2$ layer 27 is hydrated in contact with the solution 47.

Figure 8:
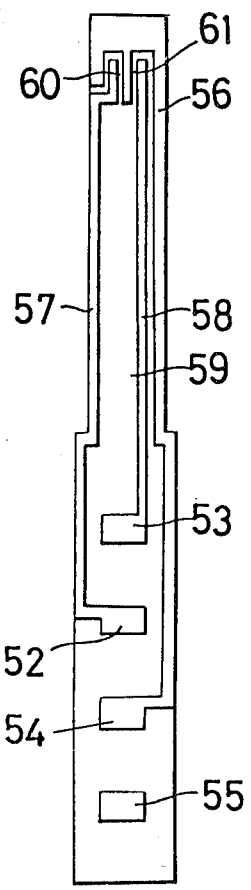
FIG. 8 is a plan view of a plural ion sensitive FET transducer according to another embodiment of the present invention.

FIG. 8 illustrates a plan view of a FET sensor for detecting and measuring a plural ion. The plural ion sensitive FET sensor is shown as having two source electrodes 52 and 53, a drain electrode 54 and substrate electrode 55. If the source and the drain regions in the plural ion sensitive FET sensor shown in FIG. 8 are formed by the use of a mask having a multi-pattern for the formation of such source and drain regions, the method of manufacturing such sensor can advantageously be simplified. The drain diffusion region, the source diffusion regions and the channel stopper layer in the sensor are respectively identified by 56, 57, 58 and 59. Reference numerals 60 and 61, however, represent respective gate regions. It is to be noted that, if one of the gate regions, for example, the gate region 60 is made of a layer of $Si_3N_4$ while the other gate region 61 is made of a layer of $Si_3N_4$ and covered with a chemical selective membrane, such as composed of a layer of doped oxide, externally of the $Si_3N_4$ layer, it will be appreciated that the FET sensor sensitive to PH and PNa can be obtained.

Although the present invention has fully been described by way of example with reference to the accompanying drawings, it is to be noted that various changes and modifications will be apparent to those skilled in the art. By way of example, the practice of the manufacturing method according to the present invention does not always necessarily require the performance of all of the process steps described with reference to FIGS. 5A to 5K. For example, where the $Si_3N_4$ layer 28 is processed by the use of the plasma etching technique, the step of formation of $SiO_2$ layer 27 by the use of the CVD method may be omitted. In addition, the step of diffusion to form the contact regions 19 and 22 may be omitted.

Furthermore, the etching of the silicon wafer 11 may be effected from one surface thereof. Yet, the sequence of the steps of the method according to the present invention may not be limited to that described hereinbefore and shown in the accompanying drawings. For example, the diffusion to form the channel stopper layer 19 may be carried out subsequent to the cutting of the silicon wafer 11 adjacent each of the reduced width sections 25. In any event, one of the essential features of the present invention resides in that the gate insulating layer is formed subsequent to the cutting of the silicon wafer 11 to form the cut-out portion 34.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for manufacturing a chemical selective field-effect transistor device, which comprises the steps of:
    forming spaced apart diffusion layers on one surface of a semiconductor wafer made of silicon, said diffusion layers having a predetermined doping polarity opposite to that of the semiconductor wafer;
    forming electroconductive channel stopper layers, one for each two of said diffusion layers, between the adjacent two of the diffusion layers except for one end portion of said diffusion layers and on said one surface of the semiconductor wafer, for avoiding formation of an electroconductive channel between said adjacent two of the diffusion layers, said channel stopper layer having a doping polarity opposite to that of the diffusion layers;

forming a cut-out portion in the semiconductor wafer so as to leave a substantially comb-shaped arrangement of elongated bodies of the semiconductor wafer in which said one end portion of the diffusion layers is located;

applying a layer of silicon dioxide over the entire surface area of the semiconductor wafer subsequent to the formation of the cut-out portion in the semiconductor wafer;

applying an electrically insulating layer sensitive to change in pH value and having an impermeability to a solution containing a particular chemical substance to which the device is exposed during measurement, over the silicon dioxide layer; and trimming the semiconductor wafer along scribing lines, to provide separate chemical sensitive field-effect transistors.

2. A method for manufacturing a chemical selective field-effect transistor device as claimed in claim 1, wherein said electrically insulating layer having the impermeability to the solution is made of silicon nitride.

3. A method for manufacturing a chemical selective field-effect transistor device as claimed in claim 1, wherein said formation of the cut-out portion in the semiconductor wafer made of a single crystal of silicon includes the step of etching the silicon dioxide layer on the semiconductor wafer and the step of etching the semiconductor wafer.

4. A method for manufacturing a chemical selective field-effect transistor device as claimed in claim 3, wherein the etching of the semiconductor wafer is carried out by the use of an aqueous solution of amine.

5. A method for manufacturing a chemical selective field-effect transistor device as claimed in claim 1, wherein a gate region is defined between each adjacent two of the diffusion layers at a position adjacent the one end portion of said diffusion layers, and further comprising the step of applying a chemical selective membrane over a portion of the surface of the electrically insulating layer overlaying the gate region.

* * * * *